United States Patent [19]
Livak et al.

[11] Patent Number: 5,945,284
[45] Date of Patent: Aug. 31, 1999

[54] LENGTH DETERMINATION OF NUCLEIC ACID REPEAT SEQUENCES BY DISCONTINUOUS PRIMER EXTENSION

[75] Inventors: Kenneth J. Livak, San Jose; Adam L. Lowe, San Francisco; Andrew J. Blasband, Redwood City, all of Calif.

[73] Assignee: The Perkin-Elmer Corporation, Foster City, Calif.

[21] Appl. No.: 08/863,437

[22] Filed: May 27, 1997

[51] Int. Cl.[6] .............................. C12Q 1/68; C07H 21/02; C07H 21/04
[52] U.S. Cl. .............................. 435/6; 536/23.1; 536/24.3
[58] Field of Search ................... 435/6; 935/76, 935/77, 78; 536/23.1, 24.3

[56] References Cited

U.S. PATENT DOCUMENTS

| | | | |
|---|---|---|---|
| 5,075,217 | 12/1991 | Weber | 435/6 |
| 5,302,509 | 4/1994 | Cheeseman . | |
| 5,367,066 | 11/1994 | Urdea et al. | 536/24.3 |
| 5,374,537 | 12/1994 | Grossman | 435/6 |
| 5,436,130 | 7/1995 | Mathies et al. | 435/6 |
| 5,541,067 | 7/1996 | Perlin | 435/6 |
| 5,580,728 | 12/1996 | Perlin | 435/6 |
| 5,610,287 | 3/1997 | Nikiforov | 536/24.3 |
| 5,650,277 | 7/1997 | Bavot et al. | 435/6 |
| 5,695,933 | 12/1997 | Schalling et al. | 435/6 |
| 5,767,259 | 6/1998 | Albagli et al. | 536/23.1 |

FOREIGN PATENT DOCUMENTS

| | | | |
|---|---|---|---|
| 2 718 753 | 4/1994 | France | C12Q 1/68 |
| 41 41 178 | 12/1991 | Germany | C12Q 1/68 |
| WO91/13075 | 9/1991 | WIPO . | |

OTHER PUBLICATIONS

Canard et al., "Catalytic editing properties of DMA polymerases," *Proc. Natl. Acad. Sci. USA* 92:10859–10863, Nov., 1995.

Metzker et al., "Termination of DNA synthesis by novel 3'–modified–deoxyribonucleoside 5'–triphosphates," *Nucleic Acids Research* 22(20):4259–4267, 1994.

Jeffreys et al., "Repeat Unit Sequence Variation in Minisatellites: A Novel Source of DNA Polymorphism for Studying Variation and Mutation by Single Molecule Analysis," *Cell* 60:473–485 Feb. 9, 1990.

The Stratagene Catalog, p. 39 (1988).
Weber et al., American J. of Human Genetics 44 :388–396 (1989).
Mansfield et al., J. of Chromatography A 781 ; 295–305 (1997).
Clemens et al., American J. of Human Genetics 49 : 951–960 (1991).
Perlin et al., American J. of Human Genetics 55 : 777–787 (1994).
Neilan et al., Bio Techniques 17(4) : 708–712 (1994).
Litt et al., Amrerican J. of Human genetics 44 : 397–401 (1997).
Matthews et al., Analytical Biochemistry 169 :1–25 (1988).
The Dynal Catalog/Technical Handbook pp. 116–119 (1995).

*Primary Examiner*—W. Gary Jones
*Assistant Examiner*—Ethan Whisenant
*Attorney, Agent, or Firm*—Paul D. Grossman

[57] ABSTRACT

In a first aspect, the method of the invention includes the steps of annealing a primer to a target nucleic acid; performing a first primer extension reaction using a first primer extension reagent; separating the target-primer hybrid and unreacted first primer extension reagent; performing a second primer extension reaction using a second primer extension reagent, wherein at least one of the first or second primer extension reagents includes an extendible nucleotide having a label attached thereto; separating the target-primer hybrid from unreacted second primer extension reagent; measuring a signal produced by the label; treating the label so as to render the label undetectable; and repeating the above steps until the signal is substantially less than a signal detected in a previous cycle. In a second aspect, the method of the invention includes the steps of annealing a primer to a target nucleic acid; performing a first primer extension reaction using a first primer-extension reagent; separating the target-primer hybrid from unreacted first primer extension reagent; performing a second primer extension reaction using a second primer extension reagent and with a primer termination reagent, the primer termination reagent including a nucleotide terminator having a label attached thereto; separating the target-primer hybrid from unreacted second primer extension reagent and unreacted primer termination reagent; measuring a signal produced by the label; and repeating the above steps until a signal is detected indicating incorporation of the nucleotide terminator. The invention further includes kits useful for practicing the above methods.

15 Claims, 6 Drawing Sheets

LENGTH DETERMINATION OF NUCLEIC ACID REPEAT SEQUENCES BY DISCONTINUOUS PRIMER EXTENSION

FIELD OF THE INVENTION

This invention relates to methods and kits useful for determining the length of nucleic acid repeat sequences. More specifically, this invention relates to methods and kits useful for determining the length of nucleic acid repeat sequences by employing a discontinuous primer extension reaction.

REFERENCES

Ausubel et al. eds., *Current Protocols in Molecular Biology Volume* 1, Chapter 2, Section I, John Wiley & Sons, New York (1993)
Barany et al., International Patent Application PCT/US91/06103
Beattie et al., *Clinical Chemistry*, 39:719–722 (1993)
Beaucage and Iyer, *Tetrahedron*, 48: 2223–2311 (1992)
Boom et al., U.S. Pat. No. 5,234,809
Bronstein, et al., *J. Biolumin. Chemilumin.*, 4: 99–111 (1990)
Caskey and Edwards, U.S. Pat. No. 5,364,759
Chidgeavadze et al., *Nuccleic Acids Research*, 12: 1671–1686 (1984); and Chidgeavadze et al., *FEB. Lett.*, 183: 275–278 (1985).
Damha et al., *Nucleic Acids Research*, 18:3813–3821 (1990)
Dieffenbach et al., in *PCR Primer: A Laboratory Manual*, Diffenbach and Dveksler, eds., p 133–142, CSHL Press, New York (1995)
Eckstein ed., *Oligonucleotides and Analogs*, Chapters 8 and 9, IRL Press (1991)
Guo et al., Nucleic Acids Research, 22(24): 5456–5465 (1994)
Jabs et al., *Proc. Natl. Acad. Sci.*, 86: 202 (1989)
Jeffreys et al., *Cell*, 60: 473 (1990)
Khan et al., U.S. patent application Ser. No. 08/696,808
Kornberg and Baker, *DNA Replication 2nd Eddition*, W. H. Freeman, New York (1991).
Kricka, in *Nonisotopic DNA Probe Techniques*, Kricka ed., Chapter 1, Academic Press (1992)
Maskos and Southern, *Nucleic Acids Research*, 20:1679–1684 (1992)
Metzker et al., *Nucleic Acids Research*, 22(20): 4259 (1994)
Miller et al., *Nucleic Acids Research*,16(3): 9–10 (1988)
Montpetit et al., *J. Virol. Methods*, 36: 119–128 (1992)
Mullis, U.S. Pat. Nos. 4,683,195; 4,683,195; and 4,683,202
Osborne, *CABIOS*, 8: 83 (1991)
Pease et al., *Proc. Natl. Acad. Sci.*, 91:5022–5026 (1994)
*Pierce Catalog and Handbook*, Pierce Chemical Co. (1994)
Pon et al., *Biotechniques*, 6:768–775 (1988)
Ruby et al., *Methods in Enzymology*, 181: 97 (1990)
Scheit, *Nucleotide Analogs*, John Wiley (1980)
Smeets et al., *Hum. Genet*, 83: 245 (1989)
Southern et al., *Genomics*, 13:1008–1017 (1992)
Walsh et al., *Biotechniques* 10(4): 506–513 (1991)
Webb, U.S. Pat. No. 4,659,774
Webber and May, *Am. J. Hum. Genet.*, 44: 388 (1989)
Williamson et al., *Cytogenet. Cell. Genet.*, 55: 457 (1990)

BACKGROUND

Methods for the analysis of genetic polymorphism have found wide utility in basic research, clinical diagnostics, forensics, and other areas. One particularly useful method of detecting genetic polymorphism is based on variations in the length of repeat sequences, such methods being variously referred to as short tandem repeat analysis (STR), variable number of tandem repeat analysis (VNTR), minisatellite analysis, and microsatellite analysis.

Detection of length polymorphisms in nucleic acid repeat sequences has up to now relied on gel electrophoresis for the determination of the length of the repeat sequence. However, gel electrophoreis has several important drawbacks in the context of repeat sequence length polymorphism analysis. First, molecular length measurements based on electrophoretic mobility are inherently imprecise due to a complicated relationship between molecular size and electrophoretic mobility. Second, the degree to which the electrophoretic process can be multiplexed is limited by the number of electrophoresis lanes and by the size of different loci run in a single lane, i.e., loci must be selected which do not electrophoretically co-migrate.

SUMMARY

The method of the present invention comprises a discontinuous primer extension reaction wherein a primer is extended in discrete increments such that in each increment of primer extension the primer is extended by an amount corresponding to a single repeat unit. Following each increment of discrete primer extension, a detection step is performed in which a modulation in a signal is detected when the primer has been extended by an amount equal to the total length of a repeat region. Thus, by counting the number of increments of discrete primer extension required to cause a modulation in the signal, the number of repeat units making up the repeat region is determined.

It is an object of the present invention to provide a precise and reproducible method for determining the number of repeat units making up a repeat region of a nucleic acid repeat sequence.

It is another object of the present invention to provide a method for determining the number of repeat units making up a repeat region of a nucleic acid repeat sequence which can perform a large number of measurements in parallel.

It is yet an additional object of the present invention to provide a method for determining the number of repeat units making up a repeat region of a nucleic acid repeat sequence which does not require an electrophoretic separation.

It is an object of the present invention to provide kits and reagents useful for practicing a method for determining the number of repeat units making up a repeat region of a nucleic acid repeat sequence having the above described characteristics.

In a first aspect, the foregoing and other objects of the invention are achieved by a method for determining the number of repeat units in a repeat region of a target nucleic acid comprising annealing a primer-complementary portion of a target nucleic acid to a primer thereby forming a target-primer hybrid; performing a first primer extension reaction using a first primer extension reagent, separating the target-primer hybrid and unreacted first primer extension reagent; performing a second primer extension reaction using a second primer extension reagent, wherein at least one of the first or second primer extension reagents includes an extendible nucleotide having a label attached thereto; separating the target-primer hybrid from unreacted second primer extension reagent; measuring a signal produced by the label; treating the label so as to render the label undetectable; and repeating the above steps until the signal is substantially less than a signal detected in a previous cycle.

In one preferred embodiment of the first aspect of the invention, the step of performing a second primer extension reaction further includes reacting the target-primer hybrid with a primer termination reagent.

In another preferred embodiment of the first aspect of the invention, the target-primer hybrid is attached to a solid support. Preferably, one of the primer or the target nucleic acid is attached to the solid support.

In yet another preferred embodiment of the first aspect of the invention, the label is a fluorescent or chemiluminescent molecule.

In another preferred embodiment of the first aspect of the invention, the label is attached to the extendible nucleotide through a cleavable linker.

In an additional preferred embodiment of the first aspect of the invention, the target nucleic acid is amplified prior to analysis. Preferably such amplification is achieved using a PCR.

In an another preferred embodiment of the first aspect of the invention, the step of treating the label so as to render the label undetectable includes either cleaving the label from the labeled extendible nucleotide or destroying a signal producing property of the label.

In a second aspect, the foregoing and other objects of the invention are achieved by a method for determining the number of repeat units in a repeat region of a target nucleic acid comprising annealing a primer-complementary portion of a target nucleic acid to a primer thereby forming a target-primer hybrid; performing a first primer extension reaction using a first primer-extension reagent; separating the target-primer hybrid from unreacted first primer extension reagent; performing a second primer extension reaction using a second primer extension reagent and with a primer termination reagent, the primer termination reagent including a nucleotide terminator having a label attached thereto; separating the target-primer hybrid from unreacted second primer extension reagent and unreacted primer termination reagent; measuring a signal produced by the label; and repeating the above steps until a signal is detected indicating incorporation of the labeled nucleotide terminator into the primer extension product.

In a preferred embodiment of the second aspect of the invention, the target-primer hybrid is attached to a solid support. Preferably, one of the primer or the target nucleic acid is attached to the solid support.

In yet another preferred embodiment of the second aspect of the invention, the label is selected from the group consisting of fluorescent and chemiluminescent molecules.

In an additional preferred embodiment of the second aspect of the invention, the target nucleic acid is amplified prior to analysis. Preferably such amplification is achieved using a PCR.

In a third aspect, the foregoing and other objects of the invention are achieved by a kit useful for determining the number of repeat units in a repeat region of a target nucleic acid comprising a primer having a sequence complementary to a primer-complementary portion of a target nucleic acid; a first primer extension reagent; and a second primer extension reagent, wherein at least one of the first or second primer extension reagents includes an extendible nucleotide having a label attached thereto.

In a preferred embodiment of the third aspect of the invention, the primer is attached to a solid support.

In an additional preferred embodiment of the second aspect of the invention, the label is selected from the group consisting of fluorescent and chemiluminescent molecules.

In another preferred embodiment of the second aspect of the invention, the label is attached to the extendible nucleotide through a cleavable linker.

These and other objects, features, and advantages of the present invention will become better understood with reference to the following description, drawings, and appended claims.

DETAILED DESCRIPTION OF THE PREFERRED EMBODIMENTS

Figure 1:
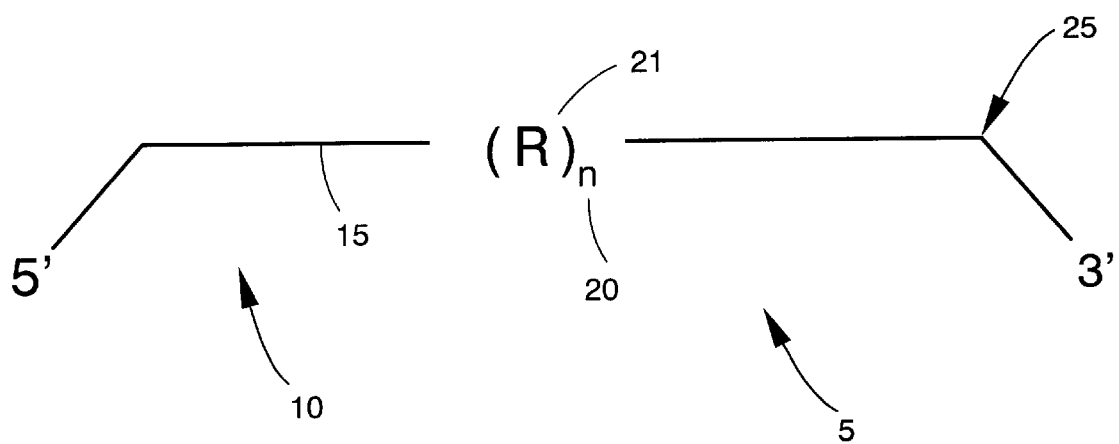
FIG. 1 shows a schematic depiction of a target nucleic acid.

Reference will now be made in detail to the preferred embodiments of the invention, examples of which are illustrated in the accompanying drawings. While the invention will be described in conjunction with the preferred embodiments, it will be understood that they are not intended to limit the invention to those embodiments. On the contrary, the invention is intended to cover alternatives, modifications, and equivalents, which may be included within the invention as defined by the appended claims.

I. DEFINITIONS

Unless stated otherwise, the following terms and phrases as used herein are intended to have the following meanings:

"Nucleoside" refers to a compound consisting of a purine, deazapurine, or pyrimidine nucleoside base, e.g., adenine, guanine, cytosine, uracil, thymine, deazaadenine, deazaguanosine, and the like, linked to a pentose at the 1' position, including 2'-deoxy and 2'-hydroxyl forms (Stryer). The term "nucleotide" as used herein refers to a phosphate ester of a nucleoside, e.g., a triphosphate ester, wherein the most common site of esterification is the hydroxyl group attached at the C-5 position of the pentose. Many times in the present disclosure the term nucleoside will be intended to include both nucleosides and nucleotides. The terms nucleotide and nucleoside as used herein are intended to include synthetic analogs having modified nucleoside base moieties, modified sugar moieties, and/or modified phosphate ester moieties, e.g., as described elsewhere (Scheit; Eckstein).

"Polynucleotide" or "oligonucleotide" refer to linear polymers of nucleotide monomers, including single, double and triple stranded deoxyribonucleotides, ribonucleotides, α-anomeric forms thereof, and the like. Usually the nucleoside monomers are linked by phosphodiester linkages, where as used herein, the term "phosphodiester linkage" refers to phosphodiester bonds or bonds including phosphate analogs thereof wherein the phosphorous atom is in the +5 oxidation state and one or more of the oxygen atoms is replaced with a non-oxygen moiety. Exemplary phosphate analogs include phosphorothioate, phosphorodithioate, phosphoroselenoate, phosphorodiselenoate, phosphoroanilothioate, phosphoranilidate, phosphoramidate, boronophosphates, and the like, including associated counterions, e.g., H, $NH_4$, Na, and the like if such counterions are present. Alternatively, polynucleotides may comprise polymers of non-nucleotidic monomers, linked through phosphodiester linkages or other linkages, which are capable of forming sequence-specific hybrids with a target nucleic acid, e.g., peptide nucleic acids (PNA) polymers. Polynucleotides typically range in size from a few monomeric units, e.g. 8–40, to several thousands of monomeric units. Whenever a polynucleotide is represented by a sequence of letters, such as "ATGCCTG," it will be understood that the nucleotides are in 5'→3' order from left to right and that "A" denotes deoxyadenosine, "C" denotes deoxycytidine, "G" denotes deoxyguanosine, and "T" denotes thymidine, unless otherwise noted.

"Extendible nucleotide" means any nucleotide that when incorporated into a primer extension product during a primer extension reaction allows for the further extension of such primer extension product. Exemplary extendible nucleotides include 2'-deoxynucleotide triphosphates, e.g., 2'-deoxyuridine-5'-triphosphate, 2'-deoxyguanosine-5'-triphosphate, 2'-deoxy-7-deazadeoxyguanosine-5'-triphosphate, 2'-deoxyadenosine-5'-triphosphate, 2'-deoxythymidine-5'-triphosphate, and 2'-deoxycytidine-5'-triphosphate. Optionally, one or more of the extendible nucleotides includes a label.

"Nucleotide terminator" means any nucleotide that when incorporated into a primer extension product prevents the further extension of such primer extension product. One requirement of a nucleotide terminator is that when the nucleotide terminator includes a ribofuranose sugar portion, the 3'-position must not have a hydroxy group capable of being subsequently used by a polymerase to incorporate additional nucleotides. Alternatively, a ribofuranose analog could be used, such as arabinose. Exemplary nucleotide terminators include 2',3'-dideoxy-β-D-ribofuranosyl, β-D-arabinofuranosyl, 3'-deoxy-β-D-arabinofuranosyl, 3'-amino-2',3'-dideoxy-β-D-ribofuranosyl, and 2',3'-dideoxy-3'-fluoro-β-D-ribofuranosyl (Chidgeavadze). Nucleotide terminators also include reversable nucleotide terminators (Metzker).

"Polymerase" means an enzyme or other catalyst capable of catalyzing a reaction leading to a target-sequence dependent incorporation of a nucleotide onto a 3'-end of a primer or primer extension product when such primer or primer extension product is annealed to a target nucleic acid. Exemplary polymerases include but are not limited to Pfu DNA polymerase, E.Coli Polymerase I, T-7 polymerase, reverse transcriptase, Taq DNA polymerase, and the like (Kornberg and Baker).

"Label" means any moiety that, when attached to a nucleotide or polynucleotide of the invention, render such nucleotide or polynucleotide detectable using known detection means. Labels may be direct labels which themselves are detectable or indirect labels which are detectable in combination with other agents. Exemplary direct labels include but are not limited to fluorophores, chromophores, radioisotopes, spin-labels, chemiluminescent labels, and the like. Exemplary indirect labels include enzymes which catalyze a signal-producing event, and ligands such as an antigen or biotin which can bind specifically with high affinity to a detectable anti-ligand, such as a labeled antibody or avidin.

"Primer extension reaction" means a reaction between a target-primer hybrid and a nucleotide which results in the addition of the nucleotide to a 3'-end of the primer such that the added nucleotide is complementary to the corresponding nucleotide of the target nucleic acid.

"Primer-extension reagent" means a reagent including components necessary to effect a primer extension reaction. Primer extension reagents typically include (i) a polymerase enzyme; (ii) a buffer; and (iii) one or more extendible nucleotides.

"Specific binding pair" refers to a pair of molecules that specifically bind to one another to form a binding complex. Examples of specific binding pairs include, but are not limited to antibody-antigen (or hapten) pairs, ligand-receptor pairs, enzyme-substrate pairs, biotin-avidin pairs, polynucleotides having complementary base pairs, and the like.

"Primer" is a polynucleotide capable of selectively annealing to a specified target sequence and thereafter serving as a point of initiation of a primer extension reaction wherein the primer is extended in a 5'→3' direction.

II. MATERIALS USED IN THE METHOD OF THE INVENTION

A. Target Nucleic Acid

A target nucleic acid for use with the invention may be derived from any living or once living organism, including but not limited to prokaryote, eukaryote, plant, animal, and virus. The target nucleic acid may originate from a nucleus of a cell, e.g., genomic DNA, or may be extranuclear nucleic acid, e.g., plasmid, mitrochondrial nucleic acid, and the like.

Many methods are available for the isolation and purification of a target nucleic acid for use in the present invention. The preferred purification method should provide target nucleic acid sufficiently free of protein to allow efficient primer extension and nucleic acid amplification. Preferred purification methods include (i) organic extraction followed by ethanol precipitation, e.g., using a phenol/chloroform organic reagent (Ausubel), preferably using an automated DNA extractor, e.g., the Model 341 DNA Extractor available from PE Applied Biosystems (Foster City, Calif.); (ii) solid phase adsorption methods (Walsh, Boom); and (iii) salt-induced DNA precipitation methods (Miller), such methods being typically referred to as "salting-out" methods. Optimally, each of the above purification methods is preceded by an enzyme digestion step to help eliminate protein from the sample, e.g., digestion with proteinase K, or other like proteases.

To increase the sensitivity of the method of the invention, preferably the target nucleic acid is amplified prior to performing the method using a suitable nucleic acid amplification procedure. Such amplification may be linear or exponential. In a preferred embodiment, amplification of the target nucleic acid is accomplished using the polymerase chain reaction (PCR) (Mullis). Generally, the PCR consists of an initial denaturation step which separates the strands of a double stranded nucleic acid sample, followed by the repetition of (i) an annealing step, which allows amplification primers to anneal specifically to positions flanking a target sequence; (ii) an extension step which extends the primers in a 5'→3' direction thereby forming an amplicon nucleic acid complementary to the target sequence, and (iii) a denaturation step which causes the separation of the amplicon and the target sequence. Each of the above steps may be conducted at a different temperature, where the temperature changes may be accomplished using a thermocycler (PE Applied Biosystems, Foster City, Calif.).

The generalized structure of a target nucleic acid for use in the present invention is shown in FIG. 1 where the target nucleic acid 5 includes a 5'-flanking portion 10 including a primer complementary portion 15, a 3'-flanking portion 25, and a repeat region 20 located between the 5'-flanking portion and the and the 3'-flanking portion. The repeat region 20 of the target nucleic acid comprises multiple repeat units $(R)_n$ 21 where R indicates a repeat unit and n designates the number of repeat units making up the repeat region. The repeat unit R may be any type of repeat motif, for example, but not limited to a microsatellite repeat (Webber and May; Smeets; Williamson), a minisatellite repeat (Jeffreys, Caskey), or an α-satellite repeat (Jabs).

The repeat region may be made up of multiple types of repeat units or repeat units which are themselves polymorphic.

B. Primer

Primers for use in the present invention are designed to obtain a balance between specificity of primer annealing, i.e., the frequency with which an undesired target sequence participates in a primer extension reaction, and efficiency of primer extension, i.e., the extent to which a desired target sequence participates in the primer extension reaction.

Specificity of primer annealing is generally controlled by the length of the primer and the temperature of the annealing reaction. Polynucleotides between about 18 and 24 bases are preferred because such polynucleotides tend to be very sequence specific when the annealing temperature is set within a few degrees of a primer melting temperature (Dieffenbach). To facilitate primer extension, a 3'-end of the primer includes an —OH group or other moiety which allows incorporation of a nucleotide onto the 3'-end of the primer. There exist a number of computer programs to facilitate primer selection in different contexts (Osborne; Montpetit).

The sequence of the primer is selected such that the primer anneals to the primer complementary portion of the 5'-flanking portion of the target nucleic acid. Preferably, the primer anneals such that a 3'-end of the primer is adjacent to a 5'-end of a repeat region of a target nucleic acid. However, the primer may also anneal to a segment of the repeat region of the target nucleic acid so long as it is at least partially anchored to the 5'-flanking portion of the target.

Preferably, primers of the invention are synthesized conventionally on an automated DNA synthesizer, e.g., PE Applied Biosystems (Foster City, Calif.) model 392 or 394 DNA/RNA Synthesizer, using standard chemistries, e.g., phosphoramidite chemistry (Beaucage). In an alternative method, primers can be isolated from a biological source.

C. Solid Phase Supports

In a preferred embodiment of the method of the invention, a target-primer hybrid is attached to a solid phase support during a separating step. Such attachment may be through either the target nucleic acid or the primer polynucleotide.

Solid phase supports for use with the invention may have a wide variety of forms, including microparticles, beads, membranes, slides, plates, micromachined chips, and the like. In addition, solid phase supports of the invention may comprise a wide variety of compositions, including glass, plastic, silicon, alkanethiolate-derivatized gold, cellulose, low cross-linked and high cross-linked polystyrene, silica gel, polyamide, and the like.

Where attachment of the target-primer hybrid is through the primer, primers may be used with a solid phase support on which they were synthesized, or they may be separately synthesized and attached to a solid phase support for use during or before the separation step of the method.

When primers are synthesized on and used with the same solid phase support, such support may comprise a variety of forms and include a variety of linking moieties. Such supports may comprise microparticles or planar arrays, or matrices of regions having substantially uniform populations of primers. A wide variety of microparticle synthesis supports may be used with the invention, including microparticles made of controlled pore glass (CPG), highly cross-linked polystyrene, acrylic copolymers, cellulose, nylon, dextran, latex, polyacrolein, and the like. Microparticle supports further include commercially available nucleoside-derivatized CPG and polystyrene beads (e.g. available from Applied Biosystems, Foster City, Calif.); derivatized magnetic beads; polystyrene grafted with polyethylene glycol (e.g., TentaGel, Rapp Polymere, Tubingen Germany); and the like. Selection of the support characteristics, such as material, porosity, size, shape, and the like, and the type of linking moiety employed depends on the conditions under which the primers are used. For example, in the present invention, supports and linkers that minimize steric hindrance of the polymerase enzymes and that facilitate access to nucleotide substrate are preferred. Other important factors to be considered in selecting the most appropriate microparticle support include size uniformity, efficiency as a synthesis support, degree to which surface area known, and optical properties, e.g., clear smooth beads provide instrumentational advantages when handling large numbers of beads on a surface.

As mentioned above, primers may also be synthesized on a single (or a few) solid phase supports to form an array of regions uniformly coated with primers. That is, within each region in such an array the same primer is synthesized. Techniques for synthesizing such arrays are disclosed elsewhere (Pease; Southern).

When primers are separately synthesized, and subsequently attached to a solid phase support for use, the primer may be attached to the support through a covalent linkage or a non-covalent linkage. When the primer is attached to the solid support through a non-covalent linkage, the primer includes one member of specific binding pair, e.g., biotin, the other member of the pair being attached to the solid support, e.g., avidin. Several methods are available for covalently linking polynucleotides to solid supports, e.g., through reaction of a 5'-amino polynucleotide with an isothiocyanate-functionalized glass support (Guo). A wide range of exemplary linking moieties for attaching primers onto solid supports either covalently or non-covalently are disclosed elsewhere. (Pon; Webb; Barany; Damha; Beattie; Maskos and Southern).

Where attachment of the primer-template hybrid is through the template nucleic acid, and the template nucleic acid is a PCR amplicon, the means for covalent or non-covalent attachment may be incorporated into a PCR primer used to effect the PCR. Thus, the PCR primer may contain a member of a specific binding pair, e.g., biotin, or a reactive moiety which can react with a functionalized solid support to form a covalent linkage, e.g., a 5'-amino group which reacts with a an isothiocyanate-functionalized glass support.

D. Labeled Nucleotides

In the methods of the present invention, one or more extendible nucleotides and/or nucleotide terminators include a label. The label is attached to the nucleotide in such a way that the label does not substantially interfere with polymerase-mediated incorporation of the labeled nucleotide in a primer extension reaction. Many alternative methods are available for labeling nucleotides in a manner suitable for use with the present invention (Kricka). In a preferred class of labeling methods, a nucleoside base of the nucleotide is modified to include a label, i.e., the N-6 position of a purine base or the C-5 position of a pyrimidine base. A particularly preferred class of labeled nucleotides are the propargylethoxyamino nucleotides (Khan).

In one preferred embodiment of the invention, a labeled extendible nucleotide is capable of being rendered undetectable, e.g., upon treatment with a suitable reagent or electromagnetic radiation. In this embodiment, the labeled extendible nucleotide may be rendered undetectable by either removing the label from the nucleotide or by destroying the signal-producing properties of the label.

Several methods are available for attaching a label to an extendible nucleotide such that the label may be easily removed. Exemplary cleavable linkers for linking a label to a nucleotide include but are not limited to (N-[4-(p- azidosalicylamido)butyl]-3'-[2'-pyridyldithio]propionamide (APDP), (bis[2-(succinimidooxycarbonyloxyl)ethyl]sulfone (BSOCOES), disuccininimdyl tartarate (DST), and ethylene glycobis-[succinimidylsuccinate] (EGS), and the like (Pierce Catalog).

Preferred labels whose signal producing properties may be destroyed upon treatment with a suitable reagent or electromagnetic radiation include fluorescent labels whose fluorescent properties may be destroyed by photodestruction through exposure to high intensity light or by chemical degradation through treatment with oxidizing chemicals, e.g., oxygen, sodium hypochlorite, permanginate and the like. Alternative preferred classes of labels include enzymes, which may be rendered undetectable by reaction with an irreversable enzyme inhibitor or by denaturation, and chemiluminescent labels which can undergo only a single light-producing transformation and are thus autodestructing.

E. First and Second Primer-Extension Reagents

The present invention includes first and second primer extension reagents that, when used according to methods of the invention, enable the extension of a primer to proceed in discrete increments of single repeat units, i.e., the primer is extended only by one repeat unit per discrete primer extension reaction cycle.

The first primer extension reagent of the invention includes a set of extendible nucleotides which allow a primer extension reaction to proceed only to the extent that a primer is extended by an amount less than a full repeat unit. Thus, depending on the particular sequence of the repeat unit, the first primer extension reagent may include a variety of possible extendible nucleotide combinations. For example, if the sequence of the repeat unit is AGCT, the first primer extension reagent could include extendible nucleotides T (complementary to A), T and C (complementary to A and G), or T and C and G (complementary to A and G and C). However, to prevent uncontrolled continuous primer extension, the first primer extension reagent may not contain all extendible nucleotides T and C and G and A.

In certain situations, it is desirable to sub-divide the first primer extension reagent into separate sub-reagents such that each sub-reagent includes extendible nucleotides sufficient to allow extension of a primer only to the extent that a sub-portion of the repeat sequence is formed. For example, if the repeat unit is ATGCCGT, one sub reagent of the first primer extension reagent could include extendible nucleotides T, A, and C, while another sub-reagent of the first primer extension reagent could include extendible nucleotides G, and C.

The second primer extension reagent of the invention includes a set of extendible nucleotides which allow a primer extension reaction to proceed only to the extent that the portion of a repeat unit not synthesized by the first primer extension reagent is synthesized. Thus, depending on the particular sequence of the repeat unit and the composition of the first primer reagent, the second primer extension reagent may include a variety of possible nucleotide combinations. Continuing the example discussed above, if the sequence of the repeat unit is AGCT and the first primer extension reagent includes extendible nucleotides T and C, the second primer extension reagent may include extendible nucleotides G and A.

F. Primer Termination Reagent

The present invention includes a primer termination reagent for causing the termination of primer extension such that once a primer extension product has reacted with the primer termination reagent, no further primer extension may be accomplished.

The primer termination reagent of the invention includes one or more nucleotide terminators, and optionally, a set of extendible nucleotides which allow a primer extension reaction to proceed only to the extent that a primer is extended by an amount less than a full repeat unit in a primer extension reaction. Thus, depending on the particular sequence of the repeat unit, the sequence of the 3'-flanking portion of the target nucleic acid, and the composition of the first and second primer extension reagents, the primer termination reagent may include a variety of possible extendible nucleotide and nucleotide terminator combinations. For example, if the sequence of the repeat unit is AGCT, and the first nucleotide of the 3'-flanking portion is G, and the first and second primer extension reagents include the extendible nucleotides T, C, G and A, the primer termination reagent would include only the nucleotide terminator C, such nucleotide terminator being complementary to the G located in the 3'-flanking portion. Alternatively, if the first and second primer extension reagents only include the extendible nucleotides T and C, the primer termination reagent would include extendible nucleotides G and A and nucleotide terminator C.

In certain aspects of the present invention, the primer termination reagent includes a labeled nucleotide terminator. The labeling of the nucleotide terminator is accomplished essentially as described above in Section D.

III. THE METHOD

Figure 2A:
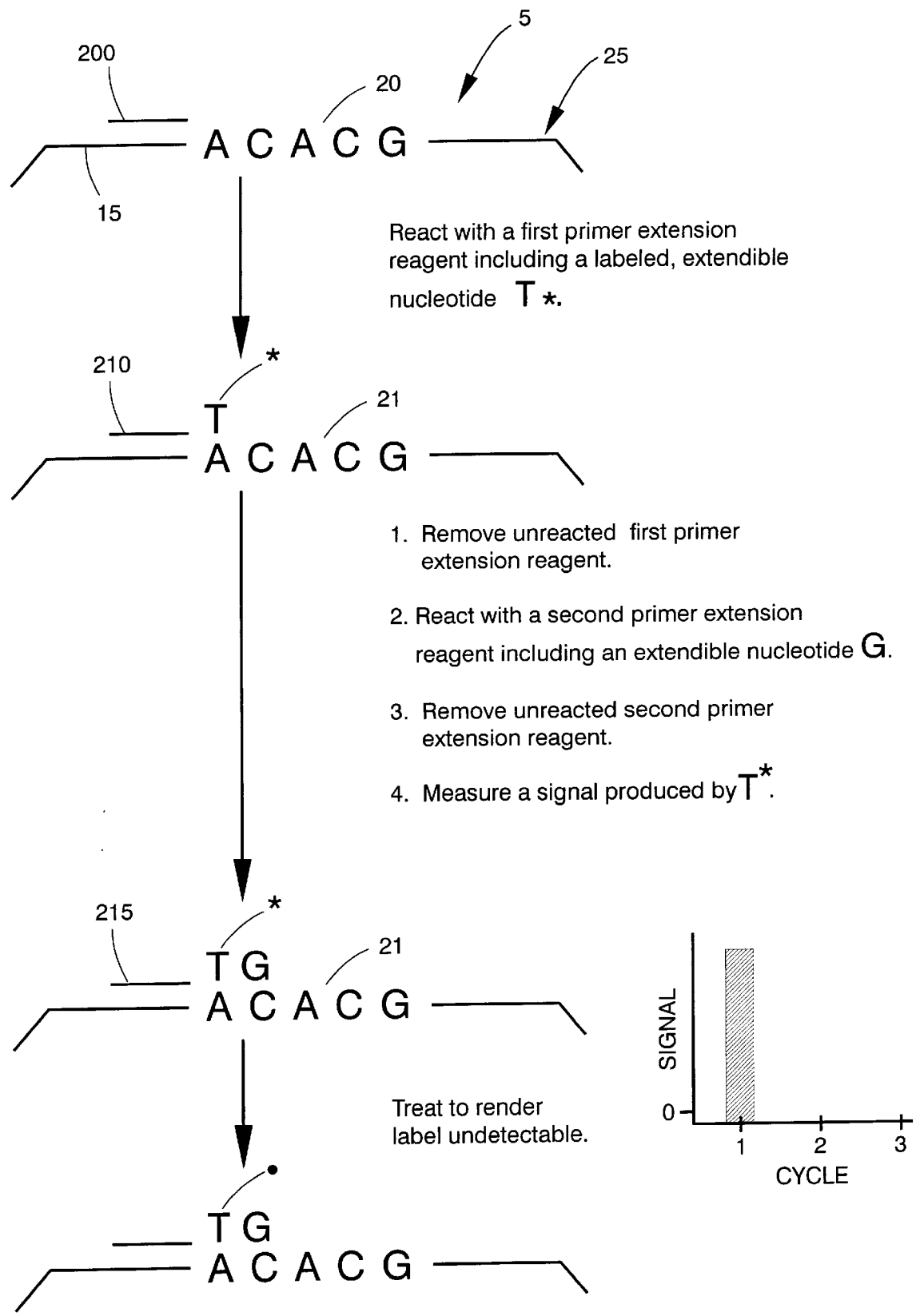
FIGS. 2A–C show a first aspect of the method of the invention wherein an extendible nucleotide is labeled and the label is rendered undetectable subsequent to each discrete increment of primer extension.
Figure 2B:
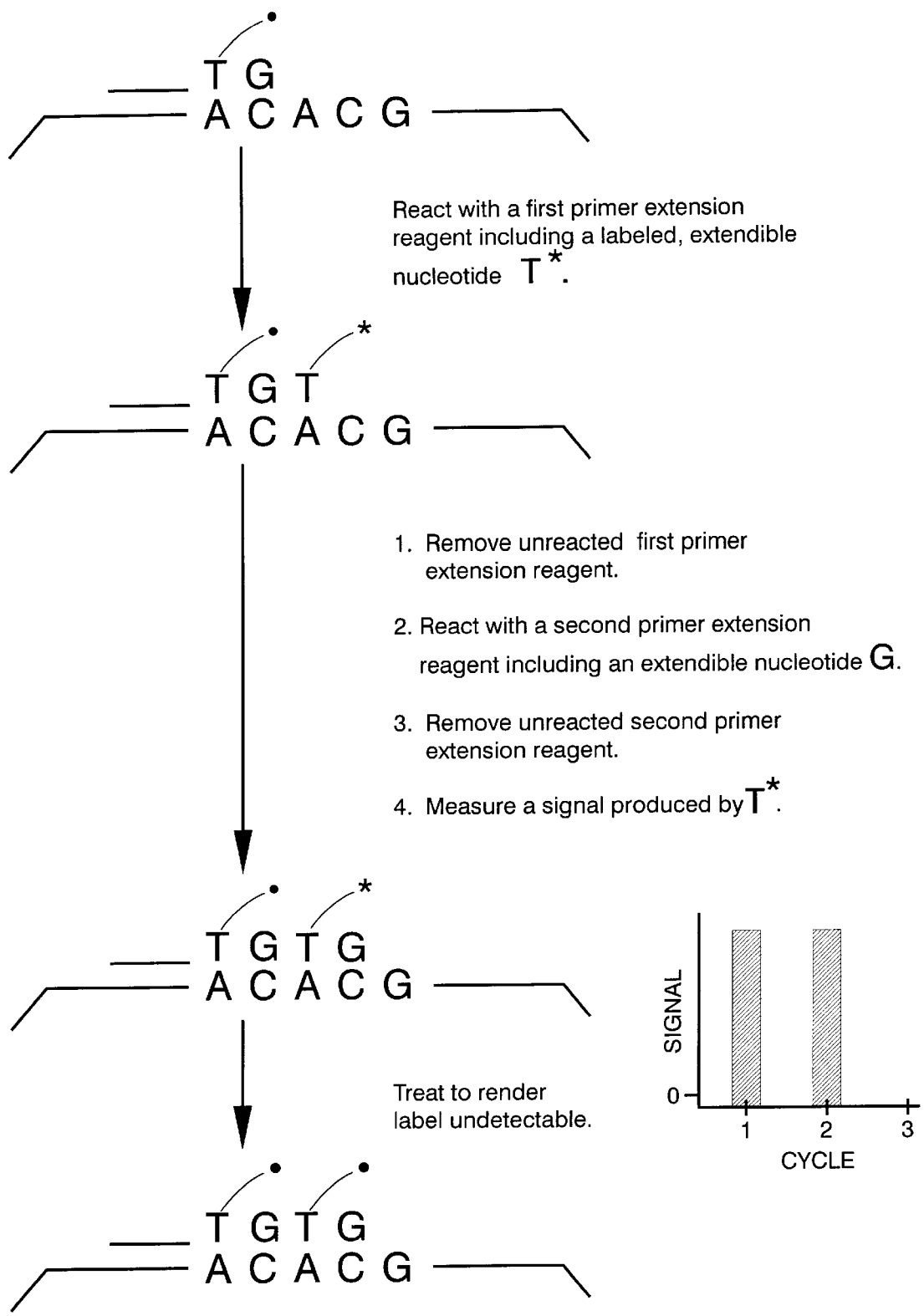
Figure 2C:
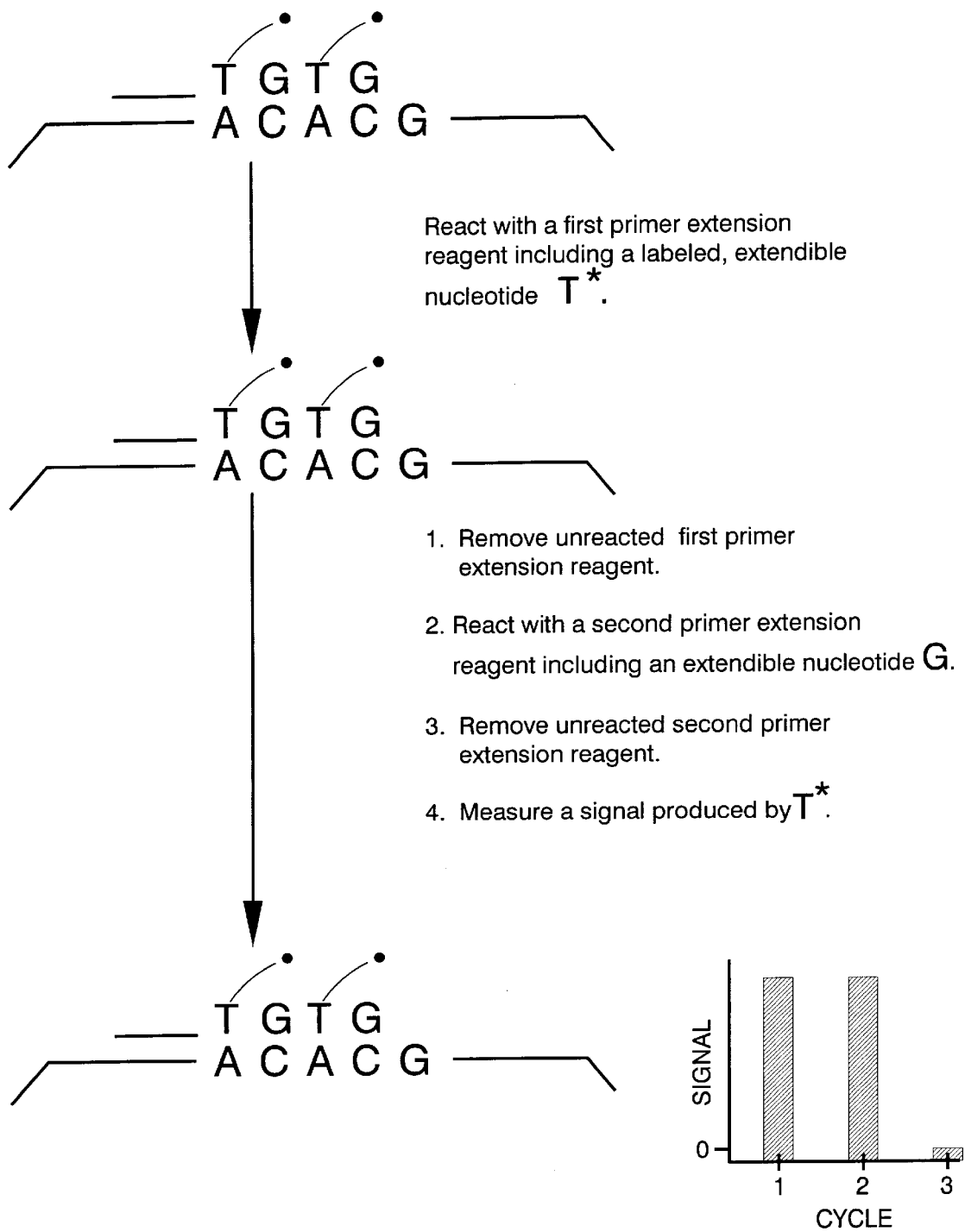

A preferred embodiment of a first aspect of the method of the invention is schematically depicted in FIGS. 2A–C. In the figure, the method is applied to a target nucleic acid 5 having a repeat region 20 made up of two copies of a two-base repeat having the sequence "AC" and a 3'-flanking portion 25 having a G nucleotide abutting the repeat region. In this preferred embodiment of the first aspect, a primer 200 is annealed to a primer-complementary portion 15 of the target nucleic acid 5 thereby forming a target-primer hybrid. The target-primer hybrid is then reacted with a first primer-extension reagent including a labeled extendible nucleotide T, resulting in the incorporation of the labeled T nucleotide into the 3'-end of a primer extension product 210. Following reaction with the first primer extension reagent, the first primer extension reagent is separated from the target-primer hybrid and the target-primer hybrid is reacted with a second primer-extension reagent including an extendible G nucleotide, resulting in the addition of the G nucleotide into a 3'-end of the primer extension product 215. Next the unreacted second primer extension reagent is separated from the target-primer hybrid and a measurement is performed to determine the amount of labeled extendible nucleotide incorporated into the primer extension product. As indicated by the histogram in the figure, at this point in the process, a large signal is detected, indicating the presence of the incorporated labeled T nucleotide. Finally, in order to prepare the target-primer hybrid for a subsequent discrete primer extension reaction cycle, the label attached to the incorporated extendible nucleotide is rendered undetectable. In the example the above described process steps are repeated two more times as shown in FIGS. 2 B and 2C. In the third cycle shown in FIG. 2C, the intensity of the measured signal is substantially reduced as compared to the signal intensities seen in the first two cycles because the labeled extendible nucleotide T can not be incorporated into the primer extension product at this point. Thus, this reduction in the measured signal seen in the third cycle indicates that the repeat region only contains two copies of the AC repeat unit.

Figure 3A:
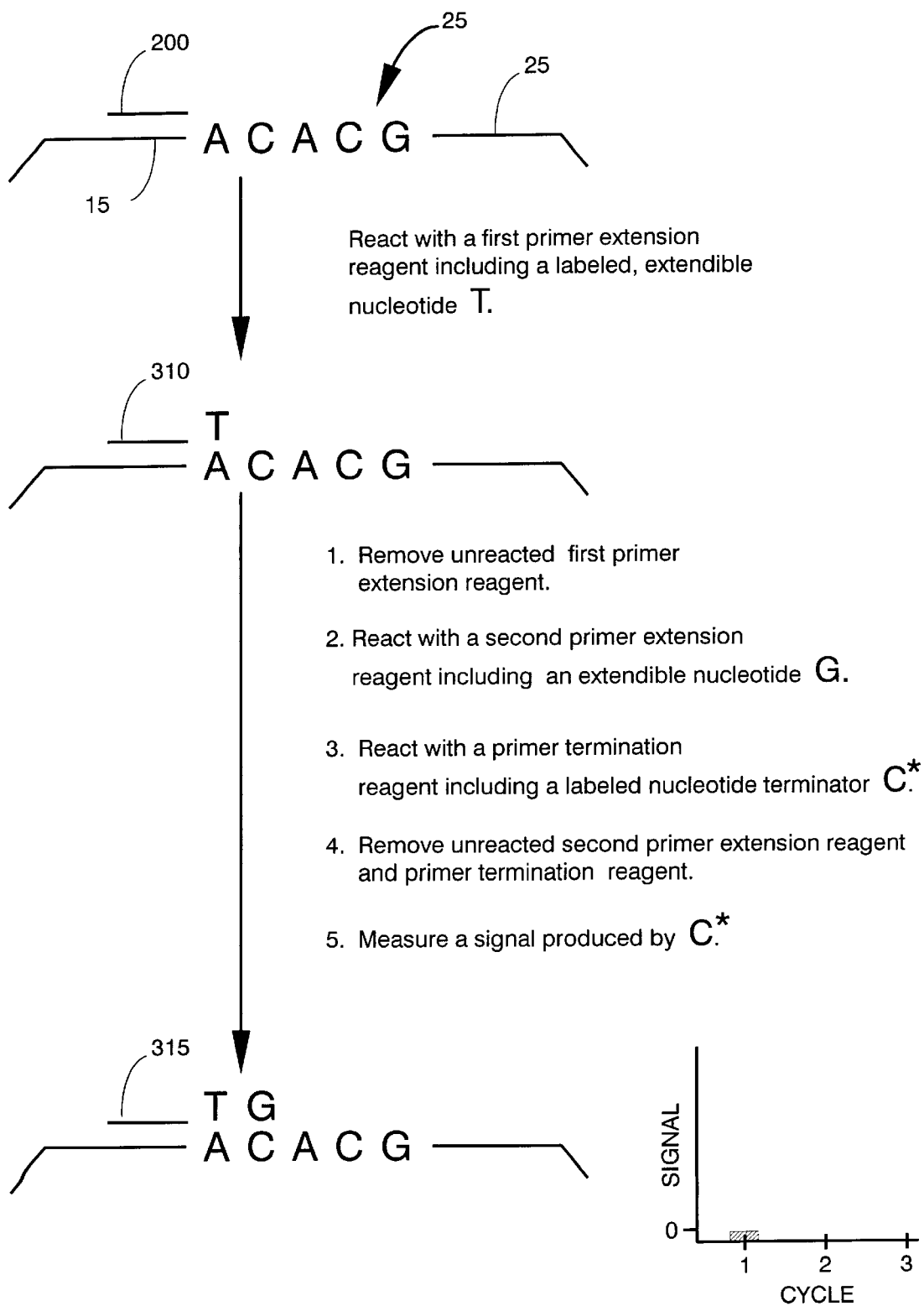
FIGS. 3A–B show a second aspect of the method of the invention wherein a nucleotide terminator is labeled.
Figure 3B:
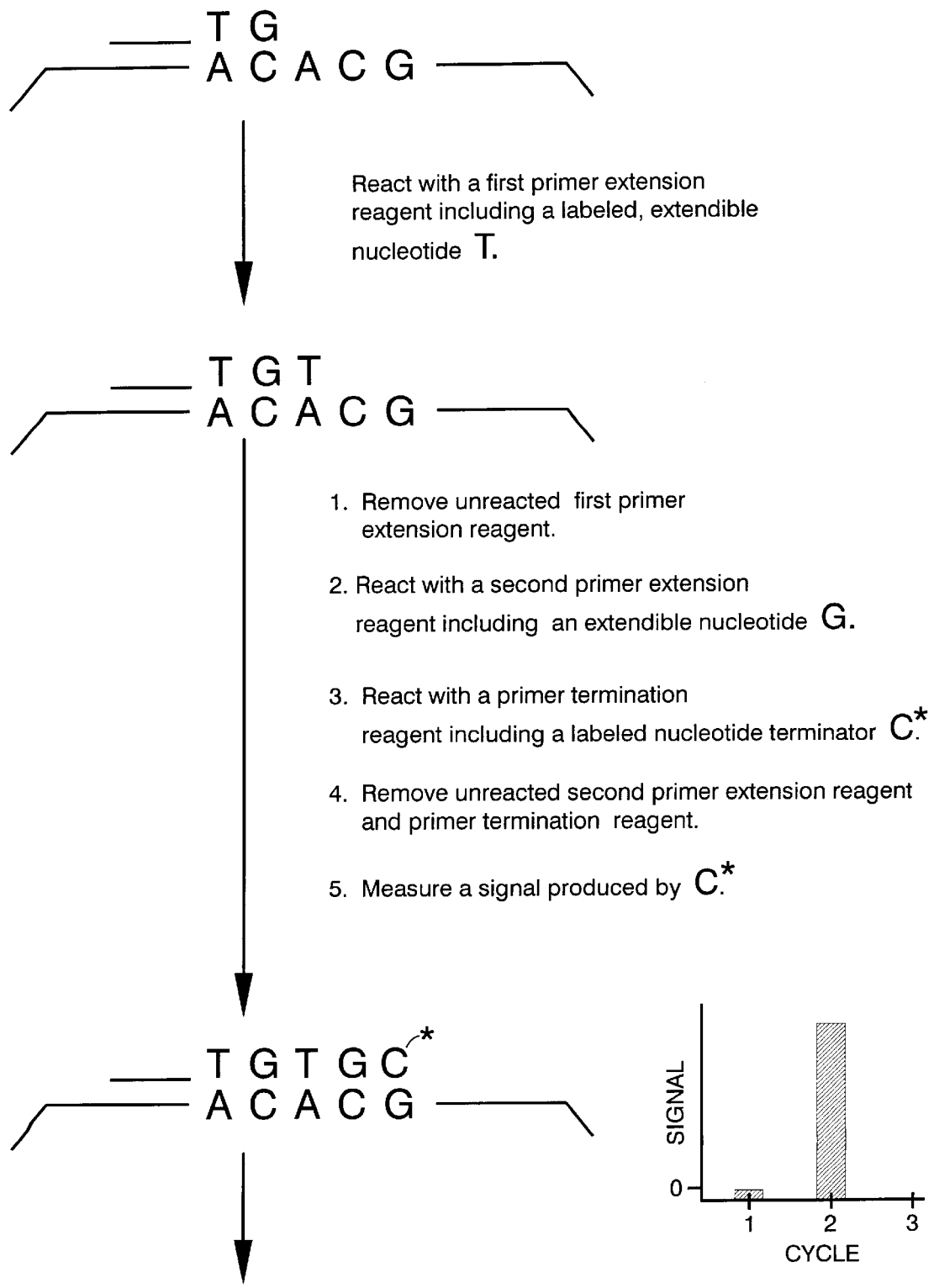

A preferred embodiment of a second aspect of the method of the invention is shown in FIGS. 3A–B. As before, the method is applied to a target nucleic acid having a repeat region made up of two copies of a two-base repeat having the sequence "AC" and a 3'-flanking portion having a G nucleotide abutting the repeat region. In this preferred embodiment of the second aspect, as before, a primer 200 is annealed to a primer-complementary portion 15 of a target nucleic acid 5 thereby forming a target-primer hybrid. The target-primer hybrid is then reacted with a first primer-extension reagent including an unlabeled extendible nucleotide T, resulting in the incorporation of the unlabeled T nucleotide into the 3'-end of a primer extension product 310. Following reaction with the first primer extension reagent, the first primer extension reagent is separated from the target-primer hybrid and the target-primer hybrid is reacted with a second primer-extension reagent, including an extendible G nucleotide, and a primer termination reagent including a labeled C nucleotide terminator, resulting in the addition of only the G extendible nucleotide into the 3'-end of the primer extension product 315. Next the unreacted second primer extension reagent and primer termination reagent are separated from the target-primer hybrid and a measurement is performed to determine the amount of labeled nucleotide terminator incorporated into the primer extension product. As indicated in the figure, at this point in the process, no signal is detected, indicating that the labeled nucleotide terminator is not incorporated into the primer extension product during this cycle of the process. In FIG. 3B, the above described process step is repeated. In this second cycle shown in FIG. 3B, the intensity of the measured signal is substantially increased as compared to the nominally zero signal intensity seen in the first step of the process because during the second step, the labeled nucleotide C terminator is incorporated into the primer extension product.

The following discussion provides a more detailed description of the above-described method steps of the first and second aspects of the invention.

A. Primer Annealing

The annealing reaction is performed under conditions which are stringent enough to guarantee sequence specificity yet sufficiently permissive to allow formation of stable hybrids at an acceptable rate. The temperature and length of time required for primer annealing depend upon several factors including the base composition, length and concentration of the primer, and the nature of the solvent used, e.g., the concentration of cosolvents such as DMSO, formamide, or glycerol, and counter ions such as magnesium. Typically, hybridization with synthetic polynucleotides is carried out at a temperature that is approximately 5 to 10° C. below the melting temperature of the target-primer hybrid in the annealing solvent. Preferably, the annealing temperature is in the range of 55 to 75° C. and the primer concentration is approximately 0.2 µM. Under these preferred conditions, the annealing reaction will be complete in only a few seconds.

B. Primer Extension Reaction

The time required to effect a primer extension reaction depends upon the length and concentration of the target sequence and upon the reaction temperature. Estimates for the rate of nucleotide addition under typical conditions vary from 35 to 100 nucleotides per second depending upon the buffer, pH, salt concentration, polymerase enzyme, and the nature of the DNA template.

In order to achieve a primer extension reaction which proceeds in discrete increments of single repeat units, according to the method of the invention, the primer extension reaction is divided into two independent steps: a first primer extension reaction and a second primer extension reaction. In the first primer extension reaction, the primer is extend by an amount less than the length of a single repeat unit, where control of the extent of primer extension is effected by the composition of a first primer extension reagent. In the second primer extension reaction, the primer is extended by an amount such that, in combination with the first primer extension reaction, the primer is extended by an amount equal to the length of a single repeat unit.

According to the first aspect of the method of the invention, one of the first or second primer extension reagents includes a labeled extendible nucleotide.

Also according to the first aspect of the method of the invention, in a variant of the above-described two-step discrete primer extension reaction, the second primer extension reagent includes a primer termination reagent. Thus, if after a second primer extension reaction the primer has been extended to the end of the repeat region of the target nucleic acid, a nucleotide terminator will be incorporated into the primer extension product thus prohibiting any further extension of that primer extension product. This is advantageous because it will remove the possibility that any spurious primer extension beyond the repeat region of the target nucleic acid will take place. This embodiment of the invention is particularly preferred where two alleles of a repeat sequence are being investigated simultaneously.

According to the second aspect of the invention, a primer termination reagent including a labeled nucleotide terminator is included in the second primer extension reaction. Preferably, the labeled nucleotide terminator is selected to be complementary to the nucleotide at the 3'-end of the 3'-flanking portion of the target nucleic acid which abuts the repeat region of such target nucleic acid.

C. Separation of Primer and Primer Extension Reagents

Between the first and second primer extension reactions, a separation step is performed to prevent the mixing of first and second primer extension reagents and thereby prevent uncontrolled primer extension. The means used to effect the separation step may be any means capable of separating the target-primer hybrid from the first and/or second primer extension reagents. Exemplary separation methods include but are not limited to HPLC, electrophoresis, liquid-liquid extraction, solid-liquid extraction, adsorption, and the like.

In a preferred embodiment, the target-primer hybrid is attached to a solid support during the separation step such that the primer extension reagents may be separated from the target-primer hybrid simply by washing the solid support. According to this embodiment, the primer may be attached to the solid support before or after performing the first primer extension reaction. The washing conditions are such that the target-primer hybrid is not substantially disrupted and nonspecific adsorption of the primer extension reagents is minimized.

D. Measuring a Signal

Subsequent to either the first or second primer extension reaction, a detection step is performed wherein the amount of intact label which has been incorporated into a primer extension product is determined. Any detection method may be used which is suitable to the type of label employed. Thus, possible detection methods include radioactive detection, optical absorbance detection, e.g., UV-visible absorbance detection, optical emission detection, e.g., fluorescence or chemiluminescence.

The measuring step can take place at various points in the process depending upon the aspect of the invention being practiced and the composition of the first and second primer extension reagents. In the first aspect, preferably the measuring step takes place after the primer extension reagent including the labeled extendible nucleotide has been reacted with and separated from the target-primer hybrid. In the second aspect, the measuring step takes place after the primer termination reagent including the labeled nucleotide terminator has been reacted with and separated from the target-primer hybrid E. Rendering A Label Undetectable According to the first aspect of the method of the invention, once a signal from a label is detected, prior to performing a subsequent cycle of discrete primer extension, the label is rendered undetectable.

In one preferred embodiment, the label is rendered undetectable by cleaving the label off of the labeled extendible nucleotide incorporated in the primer extension product. The method used for cleaving the label from the nucleotide depends on the type of cleavable linkage used to link the label and the nucleotide. See above. Exemplary cleavage reagents include thiol, base, periodate, hydroxylamine and the like. In one preferred method, the label is attached to a base-portion of a uricil nucleotide and subsequent to detection the label is cleaved off of the labeled extendible nucleotide by treatment with the enzyme uricil N-glycosylase (UNG).

In a second preferred embodiment, the label is rendered undetectable by destroying the signal-producing properties of the label itself. Depending on the type of label used, there are several methods which may be employed for destroying the signal-producing properties of the label. For example, if the label is a fluorescent dye, the label may be rendered undetectable by photobleaching the dye using an intense light source in an oxygen-rich environment. If the label is an enzyme, the label may be rendered undetectable by reacting the label with an irreversible enzyme inhibitor which renders the enzyme incapable of catalyzing a signal producing reaction. If the label is a chemiluminescent agent which can undergo only a single light-producing transformation, the label is autodistructing and thus does not require a separate reaction to render the label undetectable (Bronstein).

IV. KITS FOR PRACTICING THE METHOD

The present invention includes kits for carrying out the various aspects and embodiments of the methods of the invention. In a first aspect, kits of the invention include a primer, a first primer extension reagent, and a second primer extension reagent, wherein at least one of the first or second primer extension reagents includes an extendible nucleotide having a label attached thereto. Preferably, the label attached to the extendible nucleotide may be rendered undetectable following a treatment step effective to cleave the label from a primer extension product and/or destroy the signal producing properties of the label. Preferably, the primer is bound to a solid support, or, is capable of being bound to a solid support through a specific binding pair or through a covalent linking moiety. In another preferred embodiment, this aspect of the invention includes a solid-phase support for attachment of a target-primer hybrid through the primer or the target nucleic acid. Optionally, the kits of this first aspect of the invention include a primer termination reagent.

In a second aspect, the kits of the invention include a primer, a first primer extension reagent, a second primer extension reagent, and a primer termination reagent, wherein the primer termination reagent includes a nucleotide terminator having a label attached thereto. The second primer extension reagent and the primer termination reagent may be packaged either separately or together as a mixture. Preferably, the primer is bound to a solid support, or, is capable of being bound to a solid support through a specific binding pair or through a covalent linking moiety. In another preferred embodiment, this aspect of the invention includes a solid-phase support for attachment of a target-primer hybrid through the primer or the target nucleic acid.

All publications and patent applications refered to in this disclosure are herein incorporated by reference to the same extent as if each individual publication or patent application was specifically and individually indicated to be incorporated by reference.

Although only a few embodiments have been described in detail above, those having ordinary skill in the molecular biology art will clearly understand that many modifications are possible in the preferred embodiment without departing from the teachings thereof. Accordingly, all such modifications are intended to be encompassed within the scope of the following claims.

We claim:

1. A method for determining the number of repeat units in a repeat region of a target nucleic acid comprising the steps of:
   (a) annealing a primer-complementary portion of a target nucleic acid to a primer thereby forming a target-primer hybrid;
   (b) performing a first primer extension reaction using a first primer extension reagent;
   (c) separating the target-primer hybrid and unreacted first primer extension reagent;
   (d) performing a second primer extension reaction using a second primer extension reagent, wherein at least one of the first or second primer extension reagents includes an extendible nucleotide having a label attached thereto;
   (e) separating the target-primer hybrid from unreacted second primer extension reagent;
   (f) measuring a signal produced by the label;
   (g) treating the label so as to render the label undetectable;
   (h) repeating a cycle of steps (a) through (g) until the signal is substantially less than a signal detected in a previous cycle; and
   (i) determining a number of repeat units in a repeat region of the target nucleic acid.

2. The method of claim 1 wherein step (d) further includes reacting the target-primer hybrid with a primer termination reagent.

3. The method of claim 1 wherein the target-primer hybrid is attached to a solid support.

4. The method of claim 1 wherein the primer is attached to a solid support.

5. The method of claim 1 wherein the target nucleic acid is attached to a solid support.

6. The method of claim 1 wherein the label is selected from the group consisting of fluorescent and chemiluminescent molecules.

7. The method of claim 1 wherein the label is attached to the extendible nucleotide through a cleavable linker.

8. The method of claim 1 wherein the target nucleic acid is amplified prior to analysis.

9. The method of claim 8 wherein amplification is achieved using a PCR.

10. The method of claim 1 wherein the step of treating the label so as to render the label undetectable includes cleaving the label from the labeled extendible nucleotide.

11. The method of claim 1 wherein the step of treating the label so as to render the label undetectable includes destroying a signal producing property of the label.

12. A kit useful for determining the number of repeat units in a repeat region of a target nucleic acid comprising:

a primer having a sequence complementary to a primer-complementary portion of a target nucleic acid;

a first primer extension reagent comprising a set of extendible nucleotides that allow a primer extension reaction to proceed only to the extent that a primer is extended by an amount less than a full repeat unit; and a second primer extension reagent comprising a set of extendible nucleotides that allow a primer extension reaction to proceed only to the extent that the portion of a repeat unit not synthesized by the first primer extension reagent is synthesized;

wherein at least one of the first or second primer extension reagents includes an extendible nucleotide having a label attached thereto.

13. The kit of claim 12 wherein the primer is attached to a solid support.

14. The kit of claim 12 wherein the label is selected from the group consisting of fluorescent and chemiluminescent molecules.

15. The kit of claim 12 wherein the label is attached to the extendible nucleotide through a cleavable linker.

* * * * *